United States Patent
Healy et al.

[11] Patent Number: 6,124,451
[45] Date of Patent: Sep. 26, 2000

[54] PROCESS FOR THE PREPARATION OF SUBSTITUTED AMIDO PHTHALOCYANINE DERIVATIVES AND NOVEL SUBSTITUTED AMIDO PHTHALOCYANINE DERIVATIVES

[75] Inventors: Thomas Healy, Paisley; Cairan Thomas Ewins, Glasgow, both of United Kingdom

[73] Assignee: Ciba Specialty Chemicals Corporation, Tarrytown, N.Y.

[21] Appl. No.: 09/376,189

[22] Filed: Aug. 17, 1999

[30] Foreign Application Priority Data

Aug. 29, 1998 [GB] United Kingdom ............... 9818831

[51] Int. Cl.$^7$ .............................. C09B 47/04; C07F 1/08; C07F 3/00; C07F 15/00

[52] U.S. Cl. ..................... 540/140; 540/130; 540/135; 556/1; 556/81; 556/110; 556/118; 556/138; 556/176

[58] Field of Search ..................... 556/1, 81, 110, 556/118, 138, 176; 540/140, 130, 135

[56] References Cited

U.S. PATENT DOCUMENTS

| | | | |
|---|---|---|---|
| 4,632,703 | 12/1986 | Koike et al. | 106/22 |
| 5,177,200 | 1/1993 | Kluger et al. | 540/122 |
| 5,506,708 | 4/1996 | Harrison et al. | 359/103 |

FOREIGN PATENT DOCUMENTS

| | | |
|---|---|---|
| 0 519 395 | 12/1992 | European Pat. Off. . |
| 844419 | 8/1960 | United Kingdom . |

OTHER PUBLICATIONS

Houben–Weyl vol. 11/2, 23–24.

*Primary Examiner*—Porfirio Nazario-Gonzalez
*Attorney, Agent, or Firm*—David R. Crichton

[57] ABSTRACT

A process for the preparation of substituted amido phthalocyanines having the general formula I:

$$\text{MPc—(CONR}^1\text{R}^2)_n \qquad \text{I}$$

via the reaction of a phthalocyanine carboxamide having the formula $\text{MPc(CONH}_2)_x$ wherein Pc is a Phthalocyanine ring; M is a hydrogen or a metal capable of forming a metal phthalocyanine such as Mg, Al, Ni, Fe, Zn, Pb, Sn or Cu and x is a number from 0.1 to 4.0, with an amine acid salt denoted by formula II:

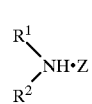

$$\text{II}$$

wherein $R^1$ and $R^2$ are independently selected from the group consisting of hydrogen; an alkyl group having 1–20 carbons; a cyclic alkyl group; an aryl group; an arylalkyl having 1–20 carbons; an alcohol group having 2–20 carbons; an alkyl amino alkyl group; an aliphatic amine having 1–20 carbons; an aliphatic amine acid salt having 1–20 carbons; polyoxyalkylene groups ranging in molecular weight 89–2000; polyoxyalkyleneamines ranging in molecular weight 148–4000; Z is the hydrogen sulphate or the hydrochloride salt of the amine.

43 Claims, No Drawings

PROCESS FOR THE PREPARATION OF SUBSTITUTED AMIDO PHTHALOCYANINE DERIVATIVES AND NOVEL SUBSTITUTED AMIDO PHTHALOCYANINE DERIVATIVES

TECHNICAL FIELD

The present invention relates to a novel process for the synthesis of substituted amido phthalocyanines and to novel substituted amido phthalocyanine derivatives.

BACKGROUND

The preparation of substituted amido phthalocyanine derivatives is well known and is described in GB 844,419 and more recently EP 0519395.

The multi-step prior art process for the production of substituted amido phthalocyanine derivatives start from the well known carboxamide of phthalocyanine. The phthalocyanine carboxamide is manufactured from a substituted phthalic acid derivative or anhydride derivative, namely trimellitic acid or anhydride. The trimellitic acid is reacted with phthalic acid or anhydride in the presence of urea, copper salt, and ammonium molybdate either in the presence of a high boiling organic solvent such as nitro benzene or ortho nitro toluene, or using excess urea as the solvent for the reaction. The ratio of trimellitic acid and phthalic acid can vary depending on the desired substitution level of the phthalocyanine carboxamide. The reaction mixture is heated at 180–250° C. for approx 4–20 hours. The reaction product thus obtained can be further purified by dilute aqueous acid wash, or by conventional acid pasting to yield a phthalocyanine carboxamide which is normally 90% pure.

The next stage of preparation is to hydrolyse the resulting amide to the acid followed by reaction of the acid group with sulphonyl chloride to produce the corresponding acid chloride. The final step in the synthesis of the amindo 755 phthalocyanines is the reaction of the acid chloride with the relevant amine.

EP0519395 describes a number of these substituted amido phthalocyanines wherein the amido substitution has a maximum of n=2, at the same time it describes the production of these derivatives from the prior art method and their use as phthalocyanine dyes and their effect in optical recording elements.

It has now been found that substituted amido phthalocyanine derivatives may be readily prepared from phthalocyanine carboxamide by reaction with amine/acid salts. This novel process involves less reaction steps than the prior art process and provides substituted amido phthalocyanine derivatives in high yield.

SUMMARY OF THE INVENTION.

The present invention relates to a process for the preparation of substituted amido phthalocyanines having the general formula I $$MPc—(CONR^1R^2)_n \qquad \qquad I$$

via the reaction of a phthalocyanine carboxamide having the formula $MPc(CONH_2)_x$ wherein Pc is a Phthalocyanine ring: M is a hydrogen or a metal capable of forming a metal phthalocyanine and x is a number from 0.1 to 4.0, preferably 1.0 to 3.0, with an amine acid salt denoted by formula II.

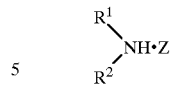

wherein $R^1$ and $R^2$ are independently selected from the group consisting of hydrogen; an alkyl group having 1–20 carbons; a cyclic alkyl group; an aryl group; an arylalkyl having 1–20 carbons; an alcohol group having 2–20 carbons; an alkyl amino alkyl group; an aliphatic amine having 1–20 carbons; an aliphatic amine acid salt having 1–20 carbons; polyoxyalkylene groups ranging in molecular weight 89–2000; polyoxyalkyleneamines ranging in molecular weight 148–4000;Z is the hydrogen sulphate or the hydrochloride salt of the amine.

It is an object of the present invention to provide a novel process for the synthesis of compounds denoted by formula I, which is less labour intensive than the multi stepped prior art process, and which readily yields products at high efficiency and purity using a relatively simple method of preparation and isolation. The scope of this novel process with regard to reactants and conditions is described herein.

It is a further object of the present invention to provide novel substituted amido phthalocyanine derivatives.

DESCRIPTION

The process according to the present invention comprises the reaction of a phthalocyanine carboxamide with an amine/acid salt to provide a substituted amido phthalocyanine.

The phthalocyanine carboxamide materials suitable for use in the present process have the general formula MPc$(CONH_2)_x$ wherein M is a hydrogen or a metal capable of forming a metal phthalocyanine and x is a number from 0.1 to 4.0. Highly preferred for use in the process of the present invention is the carboxamide of copper phthalocyanine wherein x is 1.0–3.0.

The amine acid salt materials suitable for use in the present process have the general formula II

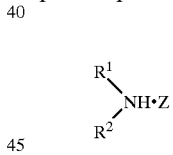

wherein $R^1$ and $R^2$ are independently selected from the group consisting of hydrogen; an alkyl group having 1–20 carbons; a cyclic alkyl group; an aryl group; an arylalkyl having 1–20 carbons; an alcohol group having 2–20 carbons; an alkyl amino alkyl group; an aliphatic amine having 1–20 carbons; an aliphatic amine acid salt having 1–20 carbons; polyoxyalkylene groups ranging in molecular weight 89–2000; polyoxyalkyleneamines ranging in molecular weight 148–4000; Z is the hydrogen sulphate or the hydrochloride salt of the amine.

Examples of $C_1$–$C_{20}$ alkyl groups suitable for use herein include: methyl, propyl, butyl, hexyl, heptyl, dodecyl, hexcadecyl, octadecyl, tert-butyl, oleyl. Preferred alkyl groups $R^1R^2$ are when $R^1$=Hydrogen and $R^2$ is dodecyl, octadecyl, hexadecyl and oleyl.

Examples of $C_5$–$C_{12}$ cyclo alkyl groups suitable for use herein include: cyclopentyl, cyclohexyl and cyclo-octyl, cyclohexyl being preferred when $R^1$=Hydrogen.

Examples of $C_7$–$C_{12}$ Aralkyl groups suitable for use herein include: benzyl or naphthylmethyl, benzyl being preferred when $R^1$=Hydrogen.

Examples of $C_6$–$C_{10}$ Aryl groups suitable for use herein include: phenyl or napthyl, with a preference for phenyl when $R^1$=Hydrogen.

The cyclic substituents $R^1$, $R^2$ namely the cylo-alkyl, aralkyl and aryl substituents may contain one or more substituent groups. Examples of suitable substituents include $C_1$–$C_8$ alkyl groups, such as methyl, ethyl, n-propyl, n-butyl and n-hexyl; $C_1$–$C_6$ alkoxy groups such as methoxy, ethoxy, n-propoxy, n-butoxy and n-hexoxy groups; hydroxy groups; nitro groups; and halogeno groups such as chloro, bromo and iodo groups.

Examples of $C_4$–$C_6$ alkyl amino alkyl groups suitable for use herein include: dimethylaminoethyl, dimethylaminopropyl, diethylaminopropylamine, dimethylaminopropyl being preffered when $R^1$=Hydrogen.

Examples of $C_2$–$C_{20}$ aliphatic amine groups suitable for use herein include: amino ethyl, amino propyl, amino butyl, amino pentyl, amino hexyl, amino heptyl, amino dodecyl amino-octyl. Preferred aliphatic amines are amino hexyl, amino heptyl, amino dodecyl and amino-octyl when $R^1$=hydrogen.

Examples of the aliphatic amine acid salt groups suitable for use herein are as specified above however as the hydrochloride or the hydrogen sulphate. The preferred amine salts being the hydrochloride amino heptyl, amino dodecyl and amino-octyl when $R^1$=Hydrogen.

Examples of $C_2$ to $C_{20}$ alcohol groups suitable for use herein include: 2-hydroxyethyl, 2-hydroxy-1,1 dimethylethyl, 3 hydroxy-2,2-dimethyl propyl, 1 hydroxy hexyl, 1 hydroxy propyl, 1 hydroxy pentyl. Preferred groups being 2 hydroxy propyl, 1 hydroxy hexyl and 1 hydroxy pentyl when $R^1$=Hydrogen.

Polyoxyalkylene groups suitable for use herein have the general structure:

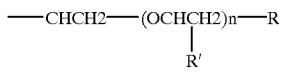

wherein R=methyl and R' can be hydrogen or methyl depending on whether ethylene oxide or propylene oxide has been used in the polymerisation reaction.

Suitable polyoxyalkylene groups include polyoxyalkylene amines having the general structure:

These materials, known as the Jeffamine Series of compounds are available from the Texaco Chemical Company under the trade names Jeffamine M89 (RTM)—Jeffamine M2070(RTM) defining mono amines and Jeffamine EDR 148 (RTM)—Jeffamine D400 (RTM) defining diamines.

Highly preferred for use as the amine acid salts in the process according to the present invention are the hydrochloride salts of the amines as hereinbefore detailed.

The phthalocyanine carboxamide can be reacted with amine salt at from an equimolar amount up to about a 100 fold excess moles, preferably 5–20 fold moles of amine salt to 1 mole of phthalocyanine carboxamide. The reaction can be carried out in the temperature range 140° C.–320° C., preferably 230–300° C. The progress of the reaction within this temperature range is rapid, however to ensure completion the reaction mixture should be heated for 0.5–20 hours, preferably 1–3 hours.

The use of high boiling organic solvents may be employed such as nitrobenzene, naphthalene, ortho-nitro toluene and mixtures thereof. The preferred method is to use the melt of the amine acid salt as the solvent. This can be done due to the very high boiling points of the amine acid salts typically in excess of 250° C., hence a melt reaction can be carried out practically and successfully within this temperature range. In most cases the isolation of the products is accomplished by separation and filtration means, as an extensive range of the amine acid salts used according to the process of the present invention are soluble in hot water. In most cases after the reaction is complete the excess amine acid salt can be removed by rinsing with hot water, before and during filtration. The use of other (water insoluble) amine acid salts requires rinsing with chloroform and ethanol to remove the excess amine salt, before filtration is carried out. Where the amine acid salts are not available in commercial form they may be readily made from the parent amine and the appropriate acid.

The present invention additionally provides novel amido substituted phthalocyanine derivatives having the general formula I:

$$MPc\text{—}(CONR^1R^2)_n \qquad\qquad I$$

wherein Pc is a Phthalocyanine ring; M is a hydrogen or a metal capable of forming a metal phthalocyanine and n is a number from 0.1 to 4.0, preferably 1.0 to 3.0; and $R^1$ and $R^2$ are indepentely selected from hydrogen; polyoxyalkylene groups ranging in molecular weight 89–2000; polyoxyalkyleneamines ranging in molecular weight 148–4000.

The following non-limiting examples further illustrate the process and products according to the present invention.

Reactions of the carboxamide of phthalocyanine and the amine acid salt go fully to completion unless specifically stated to the contrary. However the final product shows quantities of Phthalocyanine present which originates from the reaction of the trimellitic acid (anhydride) and phthalic acid (anhydride) in the production of the carboxamide.

For completeness a description of the production of mono carboxamide copper phthalocyanine  and tetra carboxamide copper phthalocyanine $CuPc(CONH_2)_4$ are included.

Preparation of $CuPc(CONH_2)_1$

A mixture of 13 g cupric chloride, 65 g of phthalic acid, 27 g of trimellitic acid and 0.4 g of ammonium molybdate were heated in the presence of 243 g of urea at about 180° C. for a period of 15 hours. The reaction mixture was then allowed to cool and dissloved in 98% H2SO4 at 60° C. with stirring, then drowned out into an ice-bath containing 500 g of ice and 3 litres of cold water, ensuring that the temperature <5° C. Filtration and washing is then carried out to yield 53 g of approx 88% pure $CuPc(CONH_2)_1$ as measured by sulphuric acid and ceric sulphate assay.

Preparation of $CuPc(CONH_2)_4$

A mixture of 13 g cupric chloride, 122 g of trimellitic anhydride and 0.4 g of ammonium molybdate were heated in the presence of 243 g of urea at about 180° C. for a period of 15 hours. The reaction mixture was then allowed to cool and dissloved in 98% H2SO4 at 60° C. with stirring, then drowned out into an ice-bath containing 500 g of ice and 3 litres of cold water, ensuring that the temperature <5° C. Filtration and washing is then carried out to yield 77 g of approx 88% pure $CuPc(CONH_2)_4$ . as measured by sulphuric acid and ceric sulphate assay.

In the following examples, the Fourier—Transform Infra—Red Spectra of both the starting material, namely CuPc7243 $(CONH_2)_x$ and each of the compounds of formula 1 according to the invention are recorded on a Philips PU9800 FTIR Spectrophotometer, as KBr discs between 4000 and 400 cm$^{-1}$. The spectra is used in conjunction with MALDI-TOF mass-spectra of the compounds of formula I to characterise both the reaction efficiency, and the reaction products.

EXAMPLE 1

Preparation of Mono Propylamido Copper Phthalocyanine 5 g of copper phthalocyanine mono carboxamide (88% Pure) and 10 g of propylamine hydrochloride were mixed well manually and heated to about 280° C. for about 1 hour using an iso-mantle. The reaction mixture was allowed to cool to about 60° C. and then reslurried by addition of water at about 80° C., filtration of the slurry and further washing with about 80° C. water was carried out to remove excess amine hydrochloride. The filtered washed product was dried at about 70° C. in an oven to give 4.52 g of mono propylamido copper phthalocyanine.

The FTIR spectrum of the CuPc carboxamide starting material and that of the final product are clearly different. Very strong peaks appear at 2900 cm$^{-1}$ and 2850 cm$^{-1}$ in the propylamido CuPc but not in that of the CuPc monocarboxamide. This is strong evidence for, and very characteristic of alkyl stretching activity which can be associated with the propyl group.

EXAMPLE 2

Preparation of Dodecylamido Copper Phthalocyanine 19.4 g of dodecylamine was placed in a round bottom flask and Hydrochloride gas bubbled continuously through the amine for about 1 hour with gentle heat about 50° C. to form dodecylamine hydrochloride. 5 g of CuPc monocarboxamide was then added all together and thoroughly mixed together manually. The mixture was heated to about 280° C. for about 2 hours. The reaction mixture was allowed to cool to room temperature then re-slurried in a minimum quantity of chloroform, and added slowly portionwise to approx 400 mls of ethanol with stirring using a magnetic stirrer. Filtration and washing with ethanol was carried out and the resultant product dried at 70° C. in an oven to give 4.69 g mono dodecylamido CuPc.

The FITR Spectrum of the CuPc carboxamide and the final product are clearly different. Very strong peaks appear at 2900 cm$^{-1}$ and 2850 cm$^{-1}$ in the dodecylamido CuPc but not in that of the CuPc monocarboxamide. This is strong evidence for, and very characteristic of alkyl stretching activity which can be associated with the dodecyl group.

MALDI-TOF mass spectra of the CuPc carboxamide and the final product are also clearly different. In the final product the mass spectra clearly shows the presence of mono dodecyl amido CuPc by an intense peak at 790 m/z. The starting material has no corresponding peaks at these mass to charge ratios.

EXAMPLE 3

Preparation of Octadecylamido Copper Phthalocyanine 5 g of copper phthalocyanine mono carboxamide 88% Pure and 32 g of octacdecylamine hydrochloride are mixed well manually and heated to about 280° C. for about 2 hours using an isomantle. The reaction mixture was allowed to cool to room temperature and the product isolated as for Example 2, to give 4.91 g mono octadecylamido CuPc.

FTIR spectra of starting material and final product were clearly different with very strong peaks at 2900 cm$^{-1}$ and 2850 cm$^{-1}$ for the final product, but not in the case of the CuPc carboxamide. This is strong evidence, and characteristic of alkyl stretching activity associated with the octadecyl group. Maldi-toff mass spectra of the final product highlights an intense peak at 874 m/z which represents mono octadecylamido CuPc. The starting material has no corresponding peaks at this mass to charge (m/z) ratio.

EXAMPLE 4

Preparation of Tetra Propylamido Copper Phthalocyanine 3.5 g of tetra carboxamide copper phthalocyanine was mixed with 18 g of propylamine hydrochloride manually and heated to about 180° C. using an oil bath for about 20 hours. The reaction mixture was then allowed to cool to room temperatureand reslurried with hot water at about 80° C., followed by filtration and washing with hot water at about 80° C. The resulting filtercake was given a final acetone wash, and dried at about 70° C. in an oven to give 3 g tetrapropylamido CuPc.

FTIR spectra clearly highlights the alkyl strech of the propyl group for tetra propylamido CuPc at 2900 cm$^{-1}$ and 2850 cm$^{-1}$. The maldi mass spectra also highlights the statistical isomeric mix of tetra substituted product eg. 794 m/z represents the mono isomer, 839 m/z represents the di isomer, 883 m/z represents the tri isomer and 925 m/z represents tetra isom.

EXAMPLE 5

Preparation of Mono Benzylamido Copper Phthalocyanine 2.0 g of mono carboxamide copper phthalocyanine was mixed manually with 5.42 g of aniline hydrochloride manually in a test tube and heated to about 300° C. for about 30 minutes using a bunsen burner. The reaction mixture was allowed to cool to room temperature and reslurried in hot water at about 80° C. to disslove excess aniline hydrochloride. Filtration and washing was carried out with hot water at about 80° C., followed by a final ethanol wash. The resultant filtercake was dried at about 70° C. in an oven to give 1.98 g of mono benzylamido CuPc.

Maldi mass spectra of the resultant product clearly shows the presence of an intense peak at 695 m/z which corresponds to mono benzylamido CuPc, this peak is not present in the starting material.

EXAMPLE 6

Preparation of Mono Phenaethylamido Copper Phthalocyanine 2.0 g of mono carboxamide copper phthalocyanine was mixed with 6.62 g of phenaethylamine hydrochloride manually in a test tube and heated to about 300° C. for about 30 minutes using a bunsen burner. The reaction mixture was allowed to cool to room temperature and reslurried in hot water at about 80° C. to disslove excess phenaethylamine hydrochloride. Filtration and washing was carried out with hot water at about 80° C. followed by a final ethanol wash. The resultant filtercake was dried at about 70° C. in an oven to give 2.2 g of mono phenaethylamido CuPc.

The FTIR spectrum of the product indicates infra red activity of a secondary amide at 1640 cm$^{-1}$ compared to the primary amide of the starting material which has activity at 1605 cm$^{-1}$. However more conclusively Maldi mass spectra of the product clearly shows an intense peak at 724.2 m/z which corresponds to mono phenaethylamido CuPc, this peak is not present in the starting material.

What is claimed is:

1. A process for the preparation of substituted amido phthalocyanines of formula $$MPc-(CONR^1R^2)_n \qquad I$$

wherein
 M is hydrogen or a metal capable of forming a metal phthalocyanine,
 Pc is a phthalocyanine radical,
 n is a number from 0.1 to 4.0,
 R$^1$ is hydrogen or R$^3$, and
 R$^2$ and R$^3$ are independently selected from the group consisting of an alkyl group having 1–20 carbons; a cyclic alkyl group; an aryl group; an arylalkyl group having from 7 to 20 carbons; a hydroxyalkyl group having from 2 to 20 carbons; an alkyl amino alkyl group or an acid salt thereof; an aliphatic aminoalkyl having from 1 to 20 carbons or an acid salt thereof; a polyoxyalkylene group of molecular weight ranging from 89 to 2000; and a polyoxyalkyleneamine of molecular weight ranging from 148 to 4000 or an acid salt thereof,
via the reaction of a phthalocyanine carboxamide having the formula $$MPc(CONH_2)_x \qquad II$$

wherein Pc and M are as defined above, and x is a number from 0.1 to 4.0,
 with an amine acid salt of formula

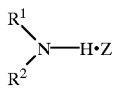 III wherein
 R$^1$ and R$^2$ are as defined above, and
 Z is sulphuric acid or hydrogen chloride.

2. A process according to claim 1 wherein M is hydrogen, Mg, Al, Ni, Fe, Zn, Pb, Sn or Cu.

3. A process according to claim 2 wherein M is Cu.

4. A process according to claim 1 or 3 wherein R$^2$ and R$^3$ are C$_1$–C$_{20}$alkyl.

5. A process according to claims 1 or 3 wherein R$^2$ and R$^3$ are C$_5$–C$_{12}$cycloalkyl.

6. A process according to claims 1, 3 or 2 wherein R$^2$ and R$^3$ are C$_7$–C$_{12}$ arylalkyl.

7. A process according to claims 1, 3 or 2 wherein R$^2$ and R$^3$ are C$_2$–C$_{20}$hydroxyalkyl.

8. A process according to any of claims 1, 3 or 2 wherein R$^2$ and R$^3$ are C$_6$–C$_{10}$aryl.

9. A process according to claims 1, 3 or 2 wherein R$^2$ and R$^3$ are C$_4$–C$_6$ alkyl amino alkyl groups or an acid salt thereof.

10. A process according to claims 1, 3 or 2 wherein R$^2$ and R$^3$ are C$_2$–C$_{20}$aliphatic aminoalkyl or an acid salt thereof.

11. A process according to claims 1, 3 or 2 wherein R$^2$ and R$^3$ are poly-ethylene oxide or poly-propylene oxide groups of molecular weight from 89 to 2000.

12. A process according to claims 1, 3 or 2 wherein R$^2$ and R$^3$ are amino-polyoxyalkylene of molecular weight from 148 to 4000 or an acid salt thereof.

13. A process according to claims 1, 3 or 2 wherein Z is hydrogen chloride.

14. A process according to claims 1, 3 or 2 wherein the ratio of amine salt of formula III to phthalocyanine carboxamide of formula II is in the molar ratio of from about 1:1 to about 100:1.

15. A process according to claims 1, 3 or 2 wherein the temperature of the melt reaction between the amine acid salt and the phthalocyanine carboxamide is from about 140° C. to about 320° C.

16. A process according to claims 1, 3 or 2 wherein the melt reaction mixture is heated for from about 0.5 to about 20 hours.

17. A phthalocyanine of formula $$MPc-(CONR^1R^2)_n \qquad I$$

wherein
 M is hydrogen or a metal capable of forming a metal phthalocyanine,
 Pc is a phthalocyanine radical,
 n is a number from 0.1 to 4.0,
 R$^1$ is hydrogen or R$^3$, and
 R$^2$ and R$^3$ are independently selected from the group consisting of a polyoxyalkylene group of molecular weight ranging from 89 to 2000; and a polyoxyalkyleneamine of molecular weight ranging from 148 to 4000 or an acid salt thereof.

18. A process according to claims 1, 3 or 2 wherein R$^2$ and R$^3$ are methyl, propyl, butyl, hexyl, heptyl, dodecyl, hexadecyl, octadecyl, tert-butyl, oleyl, cyclopentyl, cyclohexyl, cyclooctyl, benzyl, naphthylmethyl, 2-hydroxyethyl, 2-hydroxy-1,1 dimethylethyl, 3-hydroxy-2, 2-dimethyl propyl, 1-hydroxy hexyl, 2 hydroxy propyl, 1-hydroxy propyl, 1-hydroxy pentyl, phenyl, napthyl, dimethylaminoethyl, dimethylaminopropyl, diethylaminopropyl, amino ethyl, amino propyl, amino butyl, amino pentyl, amino hexyl, amino heptyl, amino octyl, amino dodecyl or —CH$_2$CH$_2$OCH$_2$CH$_2$OCH$_2$CH$_2$—NH$_2$.

19. A process according to claim 18 wherein R$^2$ and R$^3$ are dodecyl, octadecyl, hexadecyl, oleyl, 1-hydroxy hexyl, 2-hydroxy propyl, 1-hydroxy pentyl, amino hexyl, amino heptyl, amino octyl or amino dodecyl.

20. A process according to claim 18 wherein R$^1$ is hydrogen and R$^2$ is cyclohexyl, benzyl, 1-hydroxy pentyl, phenyl, dimethylaminopropyl or —CH$_2$CH$_2$OCH$_2$CH$_2$OCH$_2$CH$_2$—NH$_2$.

21. A process according to claim 14 wherein the molar ratio of III to II is from about 5:1 to about 20:1.

22. A process according to claim 15 wherein the temperature is from about 230° C. to about 300° C.

23. A process according to claim 16 wherein the melt reaction mixture is heated for from about 1 to about 3 hours.

24. A phthalocyanine according to claim 17 wherein M is hydrogen, Mg, Al, Ni, Fe, Zn, Pb, Sn or Cu.

25. A phthalocyanine according to claim 24 wherein M is Cu.

26. A phthalocyanine according to claim 17 wherein R$^2$ and R$^3$ are C$_1$–C$_{20}$alkyl.

27. A phthalocyanine according to claim 17 wherein R$^2$ and R$^3$ are C$_5$–C$_{12}$cycloalkyl.

28. A phthalocyanine according to claim 17 wherein R$^2$ and R$^3$ are C$_7$–C$_{12}$ aralkyl.

29. A phthalocyanine according to claim 17 wherein $R^2$ and $R^3$ are $C_2$–$C_{20}$ hydroxyalkyl.

30. A phthalocyanine according to claim 17 wherein $R^2$ and $R^3$ are $C_6$–$C_{10}$ aryl.

31. A phthalocyanine according to claim 17 wherein $R^2$ and $R^3$ are $C_4$–$C_6$ alkyl amino alkyl or an acid salt thereof.

32. A phthalocyanine according to claim 17 wherein $R^2$ and $R^3$ are $C_2$–$C_{20}$ aliphatic aminoalkyl or an acid salt thereof.

33. A phthalocyanine according to claim 17 wherein $R^2$ and $R^3$ are poly-ethylene oxide or poly-propylene oxide groups of molecular weight from 89 to 2000.

34. A phthalocyanine according to claim 17 wherein $R^2$ and $R^3$ are amino-polyoxyalkylene of molecular weight from 148 to 4000 or an acid salt thereof.

35. A phthalocyanine according to claim 17 wherein $R^2$ and $R^3$ are methyl, propyl, butyl, hexyl, heptyl, dodecyl, hexadecyl, octadecyl, tert-butyl, oleyl, cyclopentyl, cyclohexyl, cyclooctyl, benzyl, naphthylmethyl, 2-hydroxyethyl, 2-hydroxy-1,1 dimethylethyl, 3-hydroxy-2, 2-dimethyl propyl, 1-hydroxy hexyl, 2 hydroxy propyl, 1-hydroxy propyl, 1-hydroxy pentyl, phenyl, napthyl, dimethylaminoethyl, dimethylaminopropyl, diethylaminopropyl, amino ethyl, amino propyl, amino butyl, amino pentyl, amino hexyl, amino heptyl, amino octyl, amino dodecyl or —$CH_2CH_2OCH_2CH_2OCH_2CH_2$—$NH_2$.

36. A phthalocyanine according to claim 35 wherein $R^2$ and $R^3$ are dodecyl, octadecyl, hexadecyl, oleyl, 1-hydroxy hexyl, 2-hydroxy propyl, 1-hydroxy pentyl, amino hexyl, amino heptyl, amino-octyl or amino dodecyl.

37. A phthalocyanine according to claim 36 wherein $R^1$ is hydrogen and $R^2$ is cyclohexyl, benzyl, 1-hydroxy pentyl, phenyl, dimethylaminopropyl or —$CH_2CH_2OCH_2CH_2OCH_2CH_2$—$NH_2$.

38. A process according to claim 1 wherein x is a number from 1.0 to 3.0.

39. A process according to claim 3 wherein x is a number from 1.0 to 3.0.

40. A process according to claim 2 wherein x is a number from 1.0 to 3.0.

41. A phthalocyanine according to claim 23 wherein n is a number from 1.0 to 3.0.

42. A phthalocyanine according to claim 24 wherein n is a number from 1.0 to 3.0.

43. A phthalocyanine according to claim 23 wherein n is a number from 1.0 to 3.0.

* * * * *